United States Patent [19]
Rossen et al.

[11] Patent Number: 5,663,341
[45] Date of Patent: Sep. 2, 1997

[54] PROCESS FOR MAKING HIV PROTEASE INHIBITORS

[75] Inventors: Kai Rossen, Westfield; David Askin, Warren; Paul Reider, Westfield; Richard J. Varsolona, Scotch Plains; Ralph Volante, Cranbury, all of N.J.

[73] Assignee: Merck & Co., Inc., Rahway, N.J.

[21] Appl. No.: 487,903

[22] Filed: Jun. 7, 1995

Related U.S. Application Data

[63] Continuation of Ser. No. 192,916, Feb. 4, 1994, abandoned.

[51] Int. Cl.$^6$ .................... C07D 241/04; C07D 401/06
[52] U.S. Cl. .................... 544/388; 544/360; 544/362; 544/390
[58] Field of Search .................... 544/360, 362, 544/388, 390

[56] References Cited

U.S. PATENT DOCUMENTS

| | | | |
|---|---|---|---|
| 3,692,775 | 9/1972 | Kubanek et al. | 540/486 |
| 3,852,351 | 12/1974 | Scharpf | 564/200 |
| 5,413,999 | 5/1995 | Vacca et al. | 544/362 |

FOREIGN PATENT DOCUMENTS

| | | |
|---|---|---|
| 541168 | 5/1993 | European Pat. Off. . |

OTHER PUBLICATIONS

Kageyama et al, *Antimicrobial Agents and Chemotherapy* 36, pp. 926–933 (1992).

Lai et al, *Journal of Acquired Immune Deficiency Syndromes*, 6, pp. 24–31 (1993).

*Modern Synthetic Reactions* by Herbert House pp. 163–167, 184–189 (1965).

*Advanced Organic Chemistry* (2nd Ed), Part A by Francis Carey & Richard Sundberg, pp. 382–395 (1984).

Yoshida et al, Chemical Abstracts, vol. 106, No. 176868 (1986) (Abstract for JP 61–254545, Nov. 12, 1986).

Askin et al, *Tetrahedron Letters*, vol. 35, No. 5, pp. 673–676 (Jan. 31, 1994).

A. Neuberger, "Stereochemistry of Amino Acids," in M.L. Anson et al. (eds), Advances in Protein Chemistry vol. IV Academic Press 1948, pp. 344–356.

*Primary Examiner*—Emily Bernhardt
*Attorney, Agent, or Firm*—Mary A. Appollina; Melvin Winokur

[57] ABSTRACT

A process for racemization of optically pure or enriched piperazine-2-tert-butylcarboxamide and its derivatives comprising reacting the optically pure or enriched piperazine compound with a racemizing agent selected from a strong base, an anhydrous metal salt or a carboxylic acid, in a solvent at a temperature range of between room temperature and 250° C. The piperazine carboxamide derivatives are key intermediates in the preparation of HIV protease inhibitor compounds, including Compound J.

17 Claims, No Drawings

PROCESS FOR MAKING HIV PROTEASE INHIBITORS

This is a continuation of application Ser. No. 08/192,916 filed on Feb. 4, 1994 now abandoned.

BACKGROUND OF THE INVENTION

The present invention is concerned with a novel intermediate and process for synthesizing compounds which inhibit the protease encoded by human immunodeficiency virus (HIV), and in particular, the compound disclosed and referred to as "Compound J" in EPO 541,168, which published on May 12, 1993, or pharmaceutically acceptable salts thereof.

Compound J

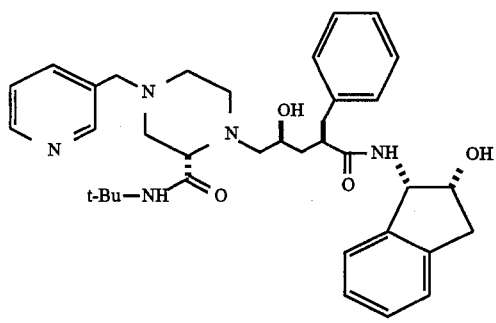

These compounds are of value in the prevention of infection by HIV, the treatment of infection by HIV and the treatment of the resulting acquired immune deficiency syndrome (AIDS).

More specifically, the instant process involves the racemization of optically pure or enriched piperazine-2-tert-butylcarboxamide and derivatives with strong base, anhydrous metal salts or carboxylic acids under mild conditions. The piperazine-tert-butylcarboxamide derivatives are key intermediates useful in the preparation of HIV protease inhibitor compounds, including Compound J.

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl, N. E. et al., *Proc. Nat'l Acad. Sci.*, 85, 4686 (1988), demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

The nucleotide sequence of HIV shows the presence of a pol gene in one open reading frame [Ratner, L. et al., *Nature*, 313, 277 (1985)]. Amino acid sequence homology provides evidence that the pol sequence encodes reverse transcriptase, an endonuclease and an HIV protease [Toh, H. et al., *EMBO J.*, 4, 1267 (1985); Power, M. D. et al., *Science*, 231, 1567 (1986); Pearl, L. H. et al., *Nature*, 329, 351 (1987)]. The end product compounds, including Compound J which is shown in Example 20 below, that can be made from the novel intermediates and process of this invention are inhibitors of HIV protease, and are disclosed in EPO 541,168, which published on May 12, 1993.

Previously, the synthesis of Compound J and related compounds was accomplished via a 12-step procedure which employed a hydroxy protected dihydro-5(S)-hydroxymethyl-3(2H) furanone which was alkylated, and involved replacement of an alcohol leaving group on the alkylated furanone with a piperidine moiety. The coupled product was then hydrolyzed to open the furanone ring into a hydroxy acid moiety, and the acid was ultimately coupled to 2(R)-hydroxy-1(S)-aminoindane. This procedure is described in EPO 541,168. The extreme length of this route (12 steps), renders this process time consuming and labor intensive, and it requires the use of many expensive reagents and an expensive starting material. A route requiring fewer reaction steps and reagents would provide desirable economical and time-saving benefits.

A modified route to Compound J and related compounds was also shown in EPO 541,168 based on the diastereoselective alkylation of the enolate derived from N-(2(R)-hydroxy-1(S)-indan-N,O-isopropyl-idene-yl)-3-phenyl-propaneamide, in which the $C_3$–$C_5$ three-carbon unit was introduced as an allyl group and later oxidized. Some problems with this route are: (a) four steps are necessary to effect the introduction of the three carbon glycidyl fragment, (b) highly toxic $OsO_4$ is used in the process and (c) low diastereoselectivity is obtained in the dihydroxylation step. Thus, a desirable process would directly introduce the three carbon unit in the correct chiral oxidized form.

Furthermore, the synthesis of the chiral piperazine intermediate was effected from 2-pyrazinecarboxylic acid in a 6 step procedure and required the use of expensive reagents such as BOC-ON and EDC. A shorter route to the piperazine intermediate which also does not use expensive reagents would thus be desired. Moreover, during the synthesis of the chiral piperazine intermediate, both the desired (S)-piperazine carboxylate enantiomer (i.e., the precursor to the 2(S)-carboxamide piperazine intermediates) and the undesired (R)-enantiomer are formed requiring separation of the desired (S)-enantiomer which is then carded on to ultimately form Compound J. In the absence of practical methodology for converting the (R)-antipode to the (S)-antipode, it was discarded as waste, thus limiting the possible efficiency of this step to 50%. Thus, a method to improve the recovery of the (S)-piperazine intermediate would be highly desirable.

More recently, a shorter route for preparing the compounds disclosed in EPO 541,168, and in particular Compound J, has been found. In this new route, 1-((R)-2',3'-Epoxypropyl-(S)-2-tert-butylcarbonyl-piperazine is prepared and reacted with N-(2(R)-hydroxy-1(S)-indan-N, O-isopropylidene-yl)-3-phenylpropaneamide to give the coupled product 8.

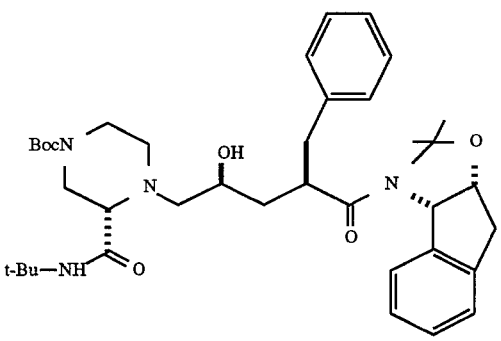

After removal of the BOC protecting group from the piperazine nitrogen, the unprotected piperazine compound is then reacted with 3-picolyl chloride to form Compound J.

As with the earlier described process for preparing the HIV protease inhibitor compounds disclosed in EPO 541, 168, preparation of the key chiral piperazine intermediate in this new process still results in a mixture of enantiomers requiring resolution of the (S)-enantiomer which is then carried on to form the final product. In the absence of practical methodology for converting the undesired (R)-antipode to the (S)-antipode, it was discarded as waste, thereby limiting the possible efficiency of this step to 50% and resulting in considerable waste and expense. Thus, a method to increase the yield of the (S)-piperazine intermediate would be highly desirable, resulting in both a reduction of the capital costs associated with the synthesis of Compound J and a reduction of the environmental problems caused by production of large quantities of unusable organic salt.

The racemization of amides and peptides under basic conditions is known, and can occur via deprotonation of the asymmetric carbon atom to form an enolate, followed by reprotonation (eq. 1).

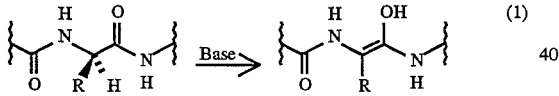

With amides bearing a heteroatom in the 2-position, racemization is also known to occur via elimination of the heteroatom followed by Michael-type readdition of the heteroatom to the unsaturated species (eq. 2). As this unsaturated species is a monomer prone to polymerization, low yields of racemized product result.

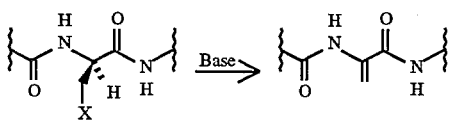

X = OR, SR, NR'R", ...

See, Advances in Protein Chemistry, Anson, M. L., Edsall, J. T., ed. Volume IV, Academic Press, New York, 1948, 344–356.

Conditions typically employed to racemize peptides, however, do not work in the case of the piperazine-2-tert-butylcarboxamide derivatives of the instant invention because the hydrogen, which is on the carbon atom of the piperazine ring, is very weakly acidic and is therefore difficult to remove. Thus, it was unexpected and unpredictable that racemization of the piperazine-2-tert-butylcarboxamides could be efficiently and rapidly carried out under mild conditions.

The instant invention provides a method for increasing the yield of the desired (S)-piperazine intermediate X, which is needed in the synthesis of Compound J, by racemizing optically pure or enriched piperazine-2-tert-butyl-carboxamide and derivatives with strong base under mild conditions. Since the optically active piperazine-2-tert-butylcarboxamides are available via resolution of the corresponding racemates, subsequent racemization of the undesired antipode provides a way to recycle it into the desired antipode, thereby increasing the yield, eliminating waste and resulting in capital savings. Thus, the instant invention provides a more advantageous method for preparing HIV protease inhibitors containing the 2(S)-carboxamide piperazine moiety than previously known by allowing a higher yielding synthesis of the compounds useful in the treatment of HIV, and in particular Compound J, by increasing recovery of the 2(S)-carboxamide piperazine intermediate.

SUMMARY OF THE INVENTION

The instant invention involves novel synthetic methods for making racemic piperazine-2-tert-butylcarboxamide derivatives, which are useful for the synthesis of HIV protease inhibitors.

The instant invention involves a process for racemization of optically pure or enriched piperazine-2-tert-butylcarboxamide substrate of formula IX or X, or a salt thereof,

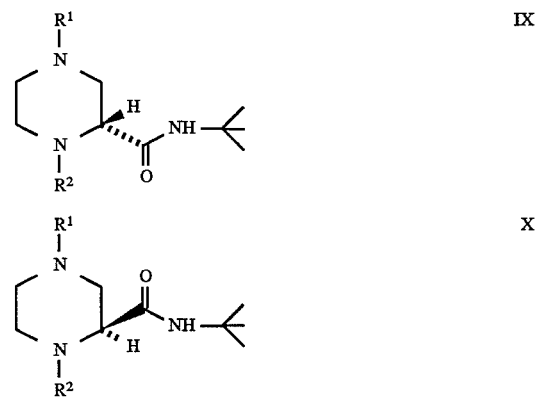

comprising reacting said substrate, or a salt thereof, with a racemizing agent selected from a strong base, an anhydrous metal salt or a carboxylic acid, in a solvent at a temperature range of between room temperature and 250° C.; wherein $R^1$ and $R^2$ are each independently selected from the group consisting of hydrogen, R,

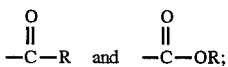

and

R is selected from the group consisting of $C_{1-5}$ alkyl, —$CH_2$-aryl, —$CH_2$-heteroaryl, aryl and trifluoromethyl.

In one embodiment of the instant invention is the process wherein $R^2$ is selected from the group consisting of hydrogen and

and

R is selected from the group consisting of $C_{1-5}$ alkyl, —$CH_2$-aryl and —$CH_2$-heteroaryl.

In one class is the process wherein said racemizing agent is a strong base selected from the group consisting of an alkyl lithium, a lithium amide, a hydroxide, an alkoxide and a Schwesinger base.

Illustrative of this class is the process wherein said strong base is selected from the group consisting of lithium tert-butoxide, sodium tert-butoxide, potassium tert-butoxide, lithium n-propoxide, sodium n-propoxide, potassium n-propoxide, sodium methoxide, potassium methoxide, sodium ethoxide and potassium ethoxide.

In a second class is the process wherein said racemizing agent is an anhydrous metal salt selected from magnesium chloride, magnesium bromide, zinc chloride, iron (III) chloride or titanium (IV) chloride.

In a third class is the process wherein said racemizing agent is a carboxylic acid selected from acetic acid, propionic acid, butyric acid or isobutyric acid.

In a subclass of each of the above is the process wherein said temperature range is between 50° and 120° C.

Illustrative of this subclass is the process wherein said solvent is an ether, an alkane, a cycloalkane, an alcohol or an aromatic compound, or a mixture thereof.

A further illustration of this subclass is the process wherein said solvent is selected from THF, cyclohexane or propanol, or a mixture thereof.

Further illustrating this subclass is the process wherein said substrate is selected from the group consisting of

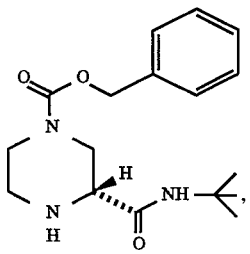

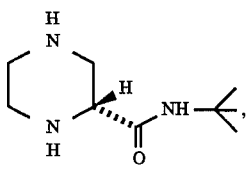

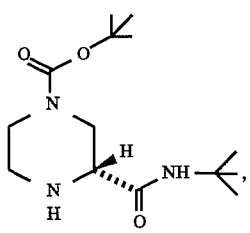

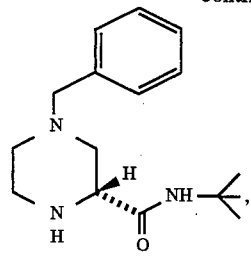

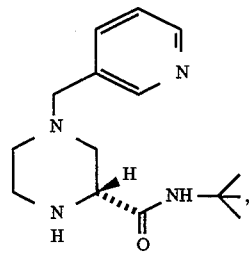

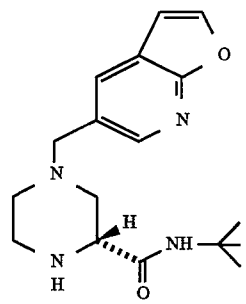

and

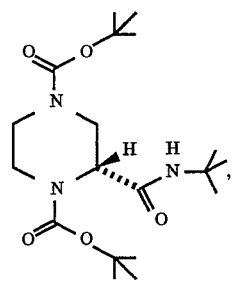

or a salt thereof.

Exemplifying this subclass is the process wherein said substrate is selected from the group consisting of

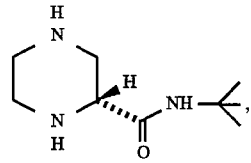

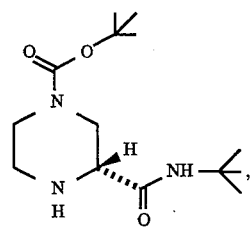

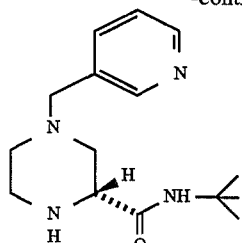

and

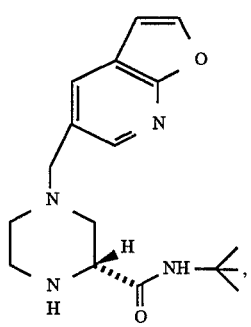

or a salt thereof.

Further exemplifying this subclass is the process wherein said substrate salt is selected from a pyroglutamic acid salt or a camphorsulfonic acid salt.

A further example is the process wherein said substrate salt is the bis-(L)-pyroglutamic acid salt.

Further exemplifying this embodiment is the process comprising the additional step of isolating the (S)-enantiomer of the piperazine-2-tert-butylcarboxamide compound from the racemate.

Still another example of the invention is a process for racemization of an optically pure or enriched piperazine-2-tert-butylcarboxamide substrate of formula IX, or a salt thereof,

IX

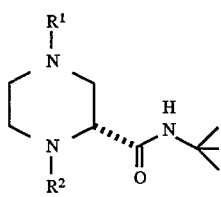

comprising reacting said substrate with an alkoxide in 1-propanol at a temperature range of between 50° and 120° C.;

wherein $R^1$ is hydrogen or tert-butyloxycarbonyl; and $R^2$ is hydrogen.

Specifically exemplifying the invention is the process wherein said alkoxide is selected from sodium n-propoxide, potassium n-propoxide and lithium n-propoxide.

More specifically exemplifying the invention is the process wherein said sodium, potassium or lithium n-propoxide is prepared in situ by the azeotropic drying of sodium, potassium or lithium hydroxide in 1-propanol.

Illustrative of the invention is the process wherein said salt is the (L)-pyroglutamic acid salt.

A more specific illustration of the invention is the process wherein the temperature range is between 85° and 120° C.

Also included within the scope of the invention are compounds of formula XI and salts thereof

XI

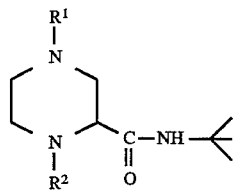

wherein $R^1$ and $R^2$ are each independently selected from the group consisting of hydrogen, R,

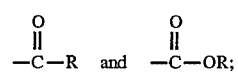

and

R is selected from the group consisting of $C_{1-5}$ alkyl, —$CH_2$-aryl, —$CH_2$-heteroaryl, aryl and trifluoromethyl.

In a second embodiment of the invention are the compounds wherein $R^1$ is selected from the group consisting of hydrogen, R and

$R^2$ is selected from the group consisting of hydrogen and

and

R is selected from the group consisting of $C_{1-5}$ alkyl, —$CH_2$-aryl and —$CH_2$-heteroaryl.

In one class of this embodiment are the compounds wherein $R^2$ is hydrogen; and R is selected from $C_{1-5}$ alkyl and —$CH_2$-heteroaryl;

provided that $R^1$ and $R^2$ are not both hydrogen and further provided that $R^1$ is not t-butyloxycarbonyl.

In a subclass are the compounds, and salts thereof, selected from the group consisting of

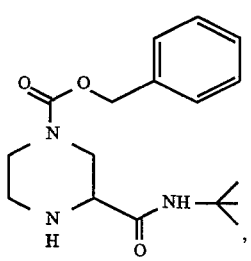

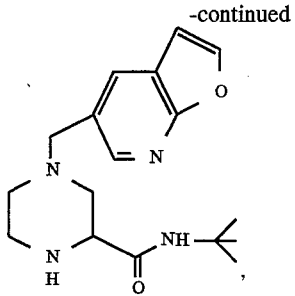

,

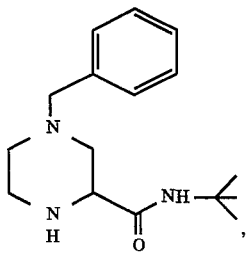

,

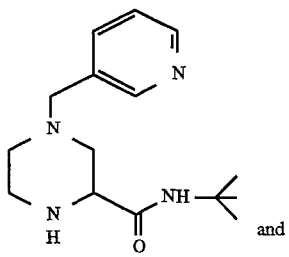

and

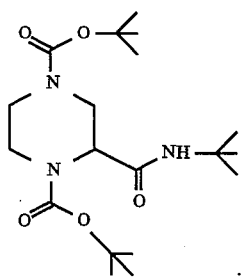

Some abbreviations that appear in this application are as follows:

| ABBREVIATIONS | |
|---|---|
| Designation | |
| | Protecting Group |
| BOC (Boc) | t-butyloxycarbonyl |
| CBZ (Cbz) | benzyloxycarbonyl (carbobenzoxy) |
| TBS (TBDMS) | t-butyl-dimethylsilyl |
| | Activating Group |
| Ts or tosyl or tosylate | p-toluenesulfonyl |
| Ns or nosyl or nosylate | 3-nitrobenzenesulfonyl |
| Tf or triflyl or triflate | trifluoromethanesulfonyl |
| Ms or mesyl or mesylate | methanesulfonyl |
| | Coupling Reagent |
| BOP reagent | benzotriazol-1-yloxytris(dimethylamino)-phosphonium hexafluorophosphate |
| BOP-Cl | bis(2-oxo-3-oxazolidinyl)phosphinic chloride |
| EDC | 1-ethyl-3-(3-dimethylaminopropyl)carbodiimide hydrochloride |

| ABBREVIATIONS | |
|---|---|
| Designation | |
| | Other |
| BOC-ON | 2-(tert-butylcarbonyloxyimino)-2-phenylacetonitrile |
| (BOC)$_2$O (BOC$_2$O or Boc$_2$O) | di-t-butyl dicarbonate |
| n-Bu$_4$N$^+$F$^-$ | tetrabutyl ammonium fluoride |
| nBuLi (n-Buli) | n-butyllithium |
| (S)-CSA | (1S)-(+)-10-camphorsulfonic acid |
| DI | deionized |
| DIEA or DIPEA | diisopropylethylamine |
| DMAP | dimethylaminopyridine |
| DME | dimethoxyethane |
| DMF | dimethylformamide |
| Et3N | triethylamine |
| EtOAc | ethyl acetate |
| h | hour(s) |
| IPA | 2-propanol |
| KF | Karl Fisher titration for water |
| LDA | lithium diisopropylamide |
| LHDMS | lithium hexamethyldisilazide |
| L-PGA | (L)-pyroglutamic acid |
| r.t. | room temperature |
| TFA | trifluoroacetic acid |
| TG | thermal gravimetry: loss on heating |
| THF | tetrahydrofuran |
| TLC | thin layer chromatography |

DETAILED DESCRIPTION OF THE INVENTION

During the synthesis of compounds which inhibit HIV protease, and in particular Compound J, which are described in EPO 541,168, published on May 12, 1993, a key intermediate is the chiral compound (S)-2-tert-butylcarboxamide piperazine 11,

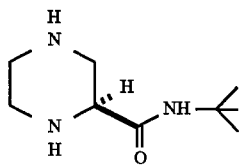

11 and its derivatives (i.e., compounds of formula X), or salts thereof. Piperazine 11 is prepared from 2-pyrazine carboxylic acid 12 by first forming the acid chloride and then reacting the pyrazine acid chloride with tert-butylamine to form the pyrazine-2-tert-butylcarboxamide 13. The pyrazine-2-tert-butylcarboxamide is then hydrogenated to form racemic-2-tert-butylcarboxamide-piperazine 14. At this point, separation of the (S)- and (R) enantiomers is necessary in order that the desired (S)-antipode may be carded on to form the HIV protease inhibitor compounds described in EPO 541,168, and in particular Compound J. Separation of the enantiomers can be effected according to methods well known to those skilled in the art, for example, chiral HPLC. Alternately, separation of the (S) and (R) enantiomers can be effected by preparing the bis (S)-camphorsulfonic acid 15 or (L)-pyroglutamic acid 16 salts of the carboxamide-piperazine compound from racemic-2-tert-butylcarboxamide-piperazine 14.

In the absence of practical methodology to convert the (R)-antipode to the desired (S)-antipode, it was discarded as waste, thereby limiting the possible efficiency of this step to 50%. The instant invention provides a method for reacting the undesired (R)-antipode with a strong base, an anhydrous metal salt or a carboxylic acid under mild conditions according to Scheme 1 to form the racemate in high yield. Once the racemate is formed, the desired (S)-antipode can be recovered according to methods known to those of ordinary skill in the art (or by using the resolution described herein), thereby increasing the efficiency and yield of the process associated with the synthesis of Compound J.

SCHEME 1

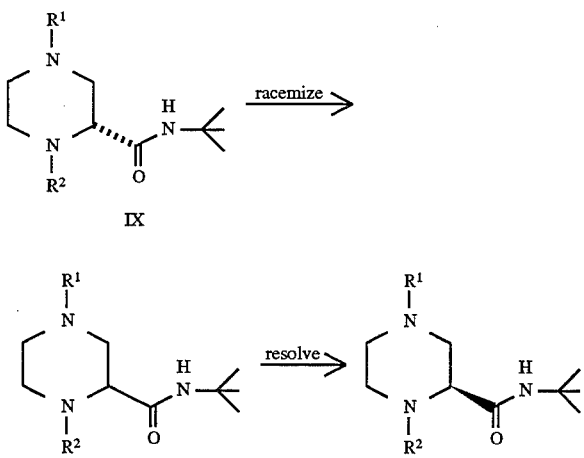

Substrates which can be used for the racemization include

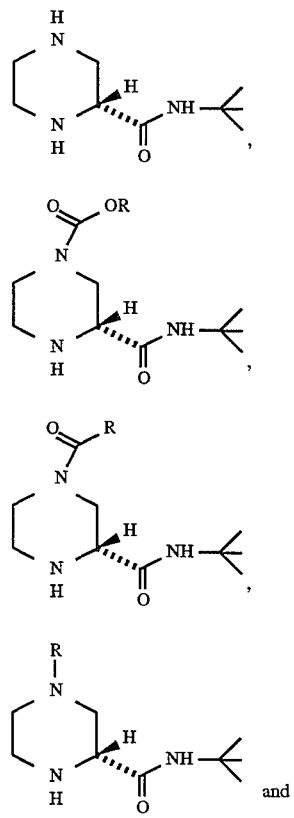

-continued

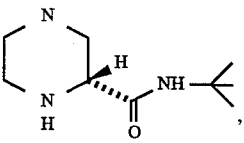

or a salt thereof, wherein R is $C_{1-5}$ alkyl, —$CH_2$-aryl, —$CH_2$-heteroaryl, aryl or trifluoromethyl.

Preferably, the following substrates, or a salt thereof, are used in the instant invention

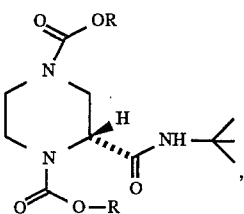

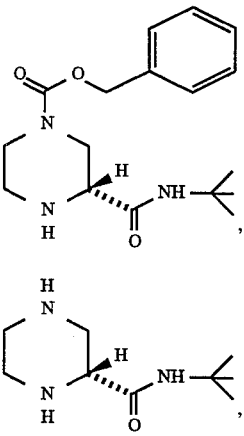

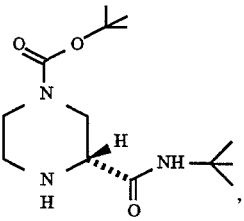

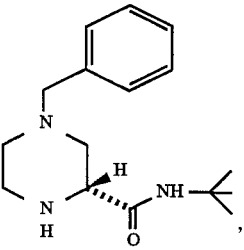

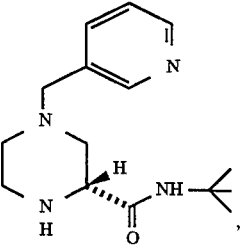

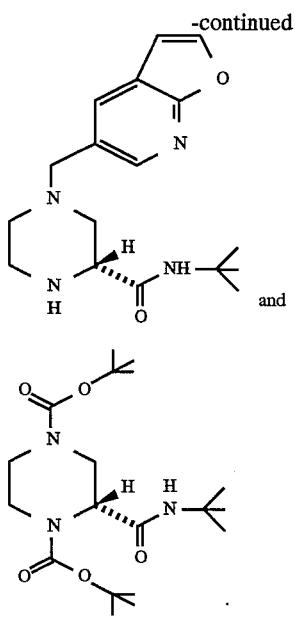

The most preferred substrates are

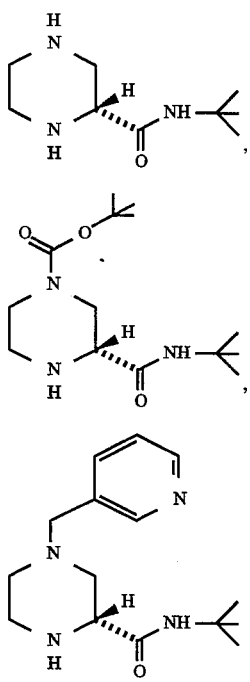

and

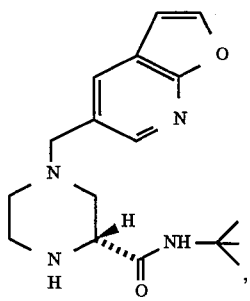

or a salt thereof.

Racemization can be effected using a racemizing agent such as anhydrous salts of Mg, Zn, Fe or Ti, carboxylic acids, or strong bases. Some examples of anhydrous metal salts which can be utilized in the instant invention are anhydrous magnesium chloride, magnesium bromide, zinc chloride, iron (III) chloride or titanium (IV) chloride. Carboxylic acids which can be used include acetic acid, propionic acid, butyric acid and isobutyric acid. Preferably, strong bases such as an alkyl lithium (e.g., methyl lithium, sec-butyl lithium, t-butyl lithium), phenyl lithium, lithium amides (e.g., LDA, LHMDS), hydroxides (e.g., lithium, sodium or potassium hydroxide), alkoxides or Schwesinger bases are employed. When the strong base is a hydroxide, it is preferable that solutions of aqueous hydroxides in alcohols be used to effect the racemization. Examples of alkoxides which can be used include lithium tert-butoxide, sodium tert-butoxide, potassium tert-butoxide, lithium n-propoxide, sodium n-propoxide, potassium n-propoxide, sodium methoxide, potassium methoxide, sodium ethoxide and potassium ethoxide. Most preferred is the use of lithium, sodium or potassium tert-butoxide or lithium, sodium or potassium n-propoxide. Most preferably, the alkoxide is generated in situ by azeotropic drying of solutions of sodium, potassium or lithium hydroxide in alcohol. See e.g., German patent DRP 558469 (1932), describing the preparation of sodium alkoxides by azeotropic drying of solutions of NaOH in alcohol.

Solvents, compatible with the reaction conditions, such as ethers, alkanes, alcohols, cycloalkanes and aromatics, or a mixture thereof, can be used. Preferably, ethers, alkanes and alcohols, or a mixture thereof, are employed as the solvents. The most preferred solvents are THF, cyclohexane and propanol, or a mixture thereof.

The racemization can be effected at a temperature range of between room temperature and 250° C. Preferably, the temperature range is between about 50° and 120° C. Most preferably, the temperature range is between about 85° and 120° C.

The instant racemization process can also be effected on salts of the substrate. Salts of tartaric acid, dibenzoyl tartaric acid, mandelic acid, lactic acid, camphorsulfonic acid and pyroglutamic acid can be used. Preferably, the (S)-camphorsulfonic acid salt or the (L)-pyroglutamic acid salts are used. The (L)-pyroglutamic acid salts are most preferred.

Representative experimental procedures utilizing the novel process are detailed below. These procedures are exemplary only and should not be construed as being limitations on the novel process of this invention.

EXAMPLE 1

Pyrazine-2-tert-butyl Carboxamide 13

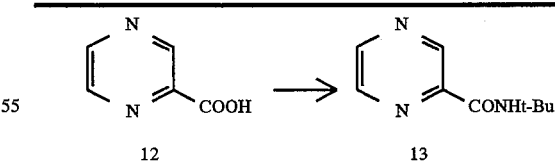

| | |
|---|---|
| 2-Pyrazinecarboxylic acid (12) | 3.35 kg (27 mol) |
| Oxalyl chloride | 3.46 kg (27.2 mol) |
| tert-Butylamine (KF = 460 µg/ml) | 9.36 L (89 mol) |
| EtOAc (KF = 56 µg/ml) | 27 L |
| DMF | 120 mL |
| 1-Propanol | 30 L |

The carboxylic acid 12 was suspended in 27 L of EtOAc and 120 mL of DMF in a 72 L 3-neck flask with mechanical stirring under $N_2$ and the suspension was cooled to 2° C. The oxalyl chloride was added, maintaining the temperature between 5° and 8° C.

The addition was completed in 5 h. During the exothermic addition, CO and $CO_2$ were evolved. The HCl that was formed remained largely in solution. Assay of the acid chloride formation was carried out by quenching an anhydrous sample of the reaction with t-butylamine. At completion <0.7% of acid 12 remained.

The reaction can be monitored by HPLC: 25 cm Dupont Zorbax RXC8 column with 1 mL/min flow and detection at 250 nm; linear gradient from 98% of 0.1% aqueous $H_3PO_4$ and 2% $CH_3CN$ to 50% aqueous $H_3PO_4$ and 50% $CH_3CN$ at 30 min. Retention times: acid 12=10.7 min, amide 13=28.1 min.

The reaction mixture was aged at 5° C. for 1 h. The resulting slurry was cooled to 0° C. and the tert-butylamine was added at such a rate as to keep the internal temperature below 20° C.

The addition required 6 h, as the reaction was very exothermic. A small portion of the generated tert-butylammonium hydrochloride was swept out of the reaction as a fluffy white solid.

The mixture was aged at 18° C. for an additional 30 min. The precipitated ammonium salts were removed by filtration. The filter cake was washed with 12 L of EtOAc. The combined organic phases were washed with 6 L of a 3% $NaHCO_3$ and 2×2 L of saturated aq. NaCl. The organic phase was treated with 200 g of Darco G60 carbon and filtered through Solka Flok and the cake was washed with 4 L of EtOAc. Carbon treatment efficiently removed some purple color in the product.

The EtOAc solution of 13 was concentrated at 10 mbar to 25% of the original volume. 30 L of 1-propanol were added, and the distillation was continued until a final volume of 20 L was reached.

The internal temperature in this solvent change was <30° C. A 1-propanol/EtOAC solution of 13 was stable to reflux at atmospheric pressure for several days.

Evaporation of an aliquot gave a tan solid m.p 87°–88° C.; $^{13}$C NMR (75 MHz, $CDCl_3$, ppm) 161.8, 146.8, 145.0, 143.8, 142.1, 51.0, 28.5.

EXAMPLE 2 rac-2-tert-Butyl-carboxamide-piperazine 14

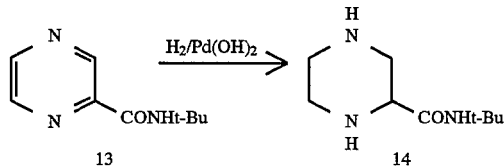

Materials

Pyrazine-2-tert-butylcarboxamide 13 (2.4 kg, 13.4 mol) in 1-Propanol solution 12 L, 20% $Pd(OH)_2/C$ 16 wt. %, water 144 g.

The pyrazine-2-tert-butylcarboxamide 13/1-propanol solution was placed into the 5 gal autoclave. The catalyst was added and the mixture was hydrogenated at 65° C. at 40 psi (3 atm) of $H_2$.

After 24 h, the reaction had taken up the theoretical amount of hydrogen and GC (gas chromatography) indicated <1% of 13. The mixture was cooled, purged with $N_2$ and the catalyst was removed by filtration through Solka Floc. The catalyst was washed with 2 L of warm 1-propanol.

The reaction was monitored by GC: 30 m Megabore column, from 100° C. to 160° C. at 10° C./min, hold 5 min, then at 10° C./min to 250° C., retention times: 13=7.0 min, 14=9.4 min. The reaction could also be monitored by TLC (thin layer chromatography) with EtOAc/MeOH (50:50) as solvent and Ninhydrin as developing agent.

Evaporation of an aliquot gave 14 as a white solid m.p. 150°–151° C.; $^{13}$C NMR (75 MHz, $D_2O$, ppm) 173.5, 59.8, 52.0, 48.7, 45.0, 44.8, 28.7.

EXAMPLE 3

(S)-2-tert-Butyl-carboxamide-piperazine bis (S)-Camphorsulfonic Acid Salt (S)-15

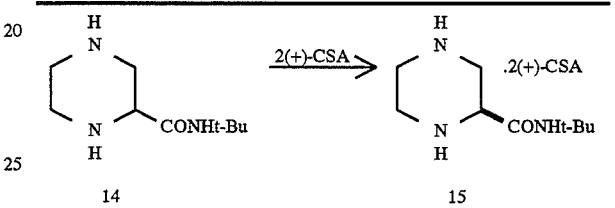

Materials

| | |
|---|---|
| rac-2-tert-Butyl-carboxamide-piperazine 14 in 1-Propanol Solution | 4.10 kg (22.12 mol) in 25.5 Kg solvent |
| (S)-(+)-10-Camphorsulfonic acid | 10.0 Kg (43.2 mol) |
| 1-Propanol | 12 L |
| Acetonitrile | 39 L |
| Water | 2.4 L |

The solution of amine 14 in 1-propanol was charged to a 100 L flask with an attached batch concentrator. The solution was concentrated at 10 mbar and a temperature <25° C. to a volume of ca 12 L.

At this point, the product had precipitated from the solution, but went back into a solution when the mixture was heated to 50° C.

Acetonitrile (39 L) and water (2.4 L) were added to give a clear, slightly brown solution.

The (S)-10-camphorsulfonic acid was charged over 30 min in 4 portions at 20° C. The temperature rose to 40° C. after the CSA was added. After a few minutes a thick white precipitate formed. The white slurry was heated to 76° C. to dissolve all the solids, the slightly brown solution was then allowed to cool to 21° C. over 8 h.

The product precipitated at 62° C. The product was filtered without aging at 21° C., and the filter cake was washed with 5 L of the $CH_3CN$/1-propanol/$H_2O$ 26/8/1.6 solvent mixture. It was dried at 35° C. in the vacuum oven with $N_2$ bleed to give 15 as a white crystalline solid m.p 288°–290° C. (with decomp.) $[\alpha]_D^{25}$=18.9° (c=0.37, $H_2O$). $^{13}$C NMR (75 MHz, $D_2O$, ppm) 222.0, 164.0, 59.3, 54.9, 53.3, 49.0, 48.1, 43.6, 43.5, 43.1, 40.6, 40.4, 28.5, 27.2, 25.4, 19.9, 19.8.

The diastereomeric excess (de) of the material was 95% according to the following chiral HPLC assay: an aliquot of 15 (33 mg) was suspended in 4 mL of EtOH and 1 mL of $Et_3N$. $Boc_2O$ (11 mg) was added and the reaction mixture was allowed to age for 1 h. The solvent was completely removed in vacuo, and the residue was dissolved in ca. 1 mL of EtOAc and filtered through a Pasteur pipet with $SiO_2$, using EtOAc as eluent. The evaporated product fractions were redissolved in hexanes at ca. 1 mg/mL. The enantiomers were separated on a Daicel Chiracell AS column with a hexane/IPA (97:3) solvent system at a flow rate of 1 mL/min and detection at 228 nm. Retention times: S antipode=7.4 min, R=9.7 min.

EXAMPLE 4

(S)-2-tert-Butylcarboxamide-4-tert-butoxycarbonyl-piperazine 1 from Salt 15

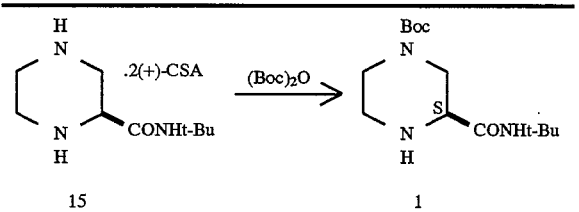

Materials

| | |
|---|---|
| (S)-2-tert-Butyl-carboxamide-piperazine Bis(S)-(+)-CSA salt 15, 95% ee | 5.54 Kg (8.53 mol) |
| Di-tert-butyl dicarbonate Lacamas | 1.86 Kg (8.53 mol) |
| $Et_3N$ Aldrich | 5.95 L (42.6 mol) |
| EtOH Punctilious 200 proof | 55 L |
| EtOAc | 2 L |

To the (S)-CSA salt 22 in a 100 L 3-neck flask with an addition funnel under $N_2$ was added EtOH, followed by triethylamine at 25° C. The solid dissolved readily on the addition of the $Et_3N$. The $Boc_2O$ was dissolved in EtOAc and charged to the addition funnel. The solution of $Boc_2O$ in EtOAc was added at such a rate as to keep the temperature below 25° C. The addition took 3 h. The reaction mixture was aged for 1 h after completion of the addition of the $Boc_2O$ solution.

The reaction can be monitored by HPLC: 25 cm Dupont Zorbax RXC8 column with 1 mL/min flow and detection at 228 nm, isocratic (50/50) $CH_3CN$/0.1M $KH_2PO_4$ adjusted to pH=6.8 with NaOH. Retention time of 1=7.2 min. The chiral assay was carried out using the same system as in the previous step. The reaction could also be monitored by TLC with a 100% EtOAc as the solvent. ($R_f$=0.7)

The solution was then concentrated to ca. 10 L at an internal temperature of <20° C. in a batch-type concentrator under 10 mbar vacuum. The solvent switch was completed by slowly bleeding in 20 L of EtOAc and reconcentrating to ca 10 L. The reaction mixture was washed into an extractor with 60 L of EtOAc. The organic phase was washed with 16 L of 5% aqueous $Na_2CO_3$ solution, 2×10 L DI water and 2×6 L of saturated aqueous sodium chloride. The combined aqueous washes were back extracted with 20 L of EtOAc and the organic phase was washed with 2×3 L water and 2×4 L of saturated aqueous sodium chloride. The combined EtOAc extracts were concentrated under 10 mbar vacuum with an internal temperature of <20° C. in a 100 L batch-type concentrator to ca. 8 L. The solvent switch to cyclohexane was achieved by slowly bleeding in ca. 20 L of cyclohexane, and reconcentrating to ca. 8 L. To the slurry was added 5 L of cyclohexane and 280 mL of EtOAc and the mixture was heated to reflux, when everything went into solution. The solution was cooled and seed (10 g) was added at 58° C. The slurry was cooled to 22° C. in 4 h and the product was isolated by filtration after a 1 h age at 22° C. The filter cake was washed with 1.8 L of cyclohexane and dried in the vacuum oven at 35° C. under $N_2$ bleed to give (>99.9 area % by HPLC, R-isomer below level of detection) 1 as a slightly tan powder. $[\alpha]_D^{25}$=22.0° (c=0.20, MeOH), m.p 107° C.; $^{13}C$ NMR (75 MHz, $CDCl_3$, ppm) 170.1, 154.5, 79.8, 58.7, 50.6, 46.6, 43.6, 43.4, 28.6, 28.3.

EXAMPLE 5

(S)-2-tert-Butyl-carboxamide-piperazine bis (L)-Pyroglutamic Acid 16

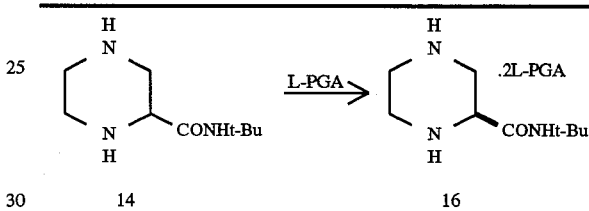

Materials

| | |
|---|---|
| rac-2-tert-butyl-carboxamide-piperazine 14 in 1-propanol solution | (0.11 mol) 155 ml, assay = 21.1 g |
| L-pyroglutamic acid | 28 g, (0.21 mol) |
| Water | 5 ml |

The solution of racemic-2-tert-butyl-carboxamide-piperazine 14 in 1-propanol was charged to a 500 ml round bottom flask with a reflux condenser, mechanical stirrer and a nitrogen inlet. Water was added along with L-pyroglutamic acid and the resulting slurry was heated to reflux. The homogeneous yellow solution was cooled to 50° C. and seeded with the bis-(L)-PGA salt of the R amine (50 mgs). Solids began forming immediately. The solution was further cooled to 25° C. and aged for 16 hours. The solids were filtered at 22° C., and the filter cake was washed with 35 ml cold 1-propanol/1% water. The filter cake was dried at 35° C. in the vacuum oven with $N_2$ bleed to give 23.74 gms (48%) of (R)-2-tert-butyl-carboxamide-piperazine bis (L)-pyroglutamic acid. The ee of the material was 98% according to the chiral HPLC assay described previously. The yellow mother liquors contained 22.6 gms (46%) of (S)-2-tert-butyl-carboxamide-piperazine bis (L)-pyroglutamic acid salt 16 and the ee was 95% according to the chiral HPLC assay. The mother liquors were evaporated and used directly in the protection step shown in Example 6.

EXAMPLE 6

(S)-2-tert-butylcarboxamide-4-tert-butoxycarbonyl-piperazine 1 from (S)-2-tert-butyl-carboxamide-piperazine bis (L)-pyroglutamic Acid Salt 16

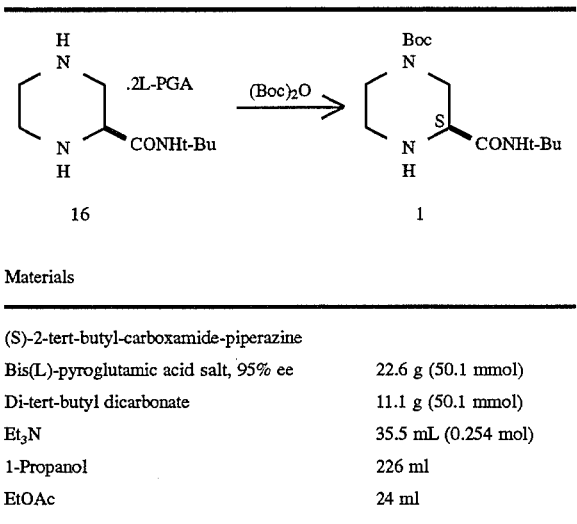

Materials

| (S)-2-tert-butyl-carboxamide-piperazine | |
|---|---|
| Bis(L)-pyroglutamic acid salt, 95% ee | 22.6 g (50.1 mmol) |
| Di-tert-butyl dicarbonate | 11.1 g (50.1 mmol) |
| Et$_3$N | 35.5 mL (0.254 mol) |
| 1-Propanol | 226 ml |
| EtOAc | 24 ml |

To (S)-2-tert-butyl-carboxamide-piperazine bis (L)-pyroglutamic acid salt in a 500 ml 3-neck flask with addition funnel under N$_2$ was added 1-propanol. The gummy yellow solid dissolved readily on the addition of the Et$_3$N. A solution of Boc$_2$O in EtOAc was added over 2 h at 22° C. The reaction mixture was aged for 1 h after completion of the addition.

The reaction can be monitored by HPLC (high performance liquid chromatography) and TLC using the same procedures as for the conversion of 15 to 1.

The solution was then concentrated and solvent switched to ethyl acetate (200 ml). The reaction mixture was washed with 50 ml of 7% aqueous Na$_2$CO$_3$ solution, 2×30 ml water and dried (Na$_2$SO$_4$) and filtered. The EtOAC solution was concentrated and solvent switched to cyclohexane (60 ml). EtOAc (1 mL) was added and the mixture was heated to reflux to dissolve all solids. The mixture was cooled and seeded (50 mg) at 52° C. The slurry was cooled to 22° C. over 2 h and the product was isolated by filtration after a 1 h age at 22° C. The filter cake was washed with 8 ml of cyclohexane and dried in the vacuum oven at 35° C. under N$_2$ bleed to give (>99.9 area % by HPLC analysis, R-isomer below level of detection) 1 as an off white powder.

EXAMPLE 7

Racemization of (S)-2-tert-butylcarboxamide-4-tert-butoxycarbonyl-piperazine 1 with Strong Base Racemization of (S)-2-tert-butylcarboxamide-4-tert-butoxycarbonyl-piperazine 1 with Strong Base

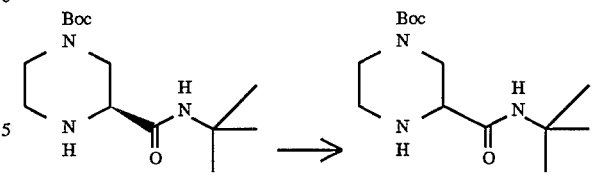

A: Racemizing Agent = Potassium tert-butoxide

| (S)-2-tert-butylcarboxamide-4-tert-butyloxycarbonyl-piperazine 1 (99.4% ee) | 0.416 g |
|---|---|
| Potassium-tert-butoxide in tert-butanol 1M | 0.04 mL |
| Cyclohexane | 7.3 mL |

To a slurry of the enantiomerically pure piperazine derivative (1) in cyclohexane was added the potassium-tert-butoxide and it was then heated to reflux for 1 hour. After cooling to r.t. a white precipitate formed which was filtered off to give 405 mg of racemic 2-tert-butylcarboxamide-4-tert-butyloxycarbonyl-piperazine.

| B: Racemizing Agent = n-Butyl lithium | |
|---|---|
| (S)-2-tert-butylcarboxamide-4-tert-butyloxycarbonyl-piperazine (99.4% ee) | 0.421 g |
| n-Butyl lithium in Cyclohexane 2.0M | 0.37 mL |
| Cyclohexane | 7.5 mL |

To the slurry of enantiomerically pure piperazine derivative (1) in cyclohexane was added slowly, with ice cooling, the solution of n-butyl lithium. The mixture was heated to reflux over night. Removal of an aliquot and analysis indicated that the ee had eroded to 50%.

| C: Racemizing Agent = Schwesinger Base | |
|---|---|
| (S)-2-tert-butylcarboxamide-4-tert-butyloxycarbonyl-piperazine (99.4% ee) | 0.342 g |
| 1-tert-Octyl-4,4,4-Tris(dimethylamino)-2,2-bis[tris-(dimethylamino)-phosphoranylideneamino]-2,4-catenadi-(phosphazene) 1M in hexane (Schwesinger base) | 0.09 mL |
| Methylcyclohexane | 6 mL |

The enantiomerically pure piperazine derivative (1) was heated to reflux with the Schwesinger base for 14 hours. Removal of an aliquot showed that the enantiomeric excess had eroded to 52%.

EXAMPLE 8

Racemization of (S)-2-tert-butylcarboxamide-4-tert-butoxycarbonyl-piperazine 1 with Carboxylic Acid

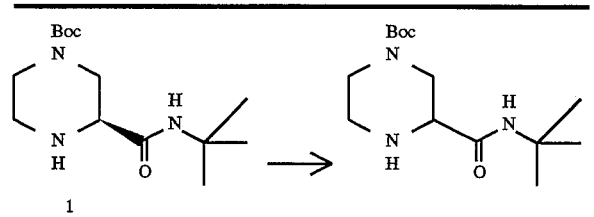

Racemizing Agent = Acetic acid

| | |
|---|---|
| (S)-2-tert-butylcarboxamide-4-tert-butyloxycarbonyl-piperazine 1 (99.4% ee) | 0.441 g |
| acetic acid | 7.73 mL |

The enantiomerically pure piperazine derivative (1) was heated in acetic acid to 100° C. for 12 hours. After cooling to 22° C., the acetic acid was removed by evaporation in vacuo to give 430 mg of a white solid. Determination of the ee showed an erosion to 68%.

EXAMPLE 9

Racemization of (S)-2-tert-butylcarboxamide-4-tert-butoxycarbonyl-piperazine 1 with Anhydrous Metal Salt

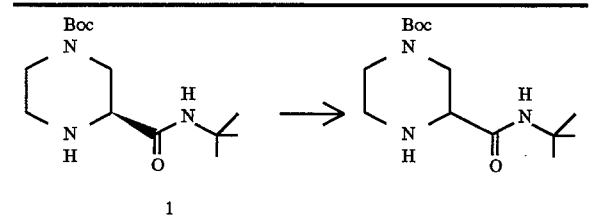

Racemizing Agent = Magnesium chloride

| | |
|---|---|
| (S)-2-tert-butylcarboxamide-4-tert-butyloxycarbonyl-piperazine 1 (99.4% ee) | 0.430 g |
| Magnesium chloride anhydrous | 0.03 g |
| Ethyleneglycol diethylether | 50 mL |

The enantiomerically pure piperazine derivative (1) and anhydrous magnesium chloride was heated for 12 h to 100° C. in the ethyleneglycol diethylether. Removal of an aliquot and analysis indicated that the ee had eroded to 97%.

EXAMPLE 10

Racemization of (S)-2-tert-butylcarboxamide-piperazine bis [(1S)-camphor-10-sulfonic Acid] 15 with Strong Base

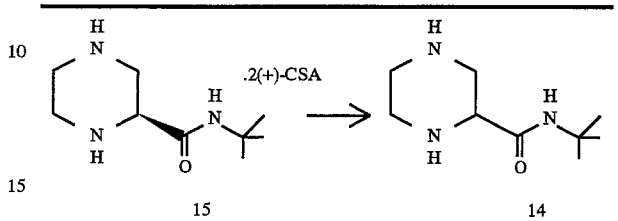

Racemizing Agent = Potassium tert-butoxide

| | |
|---|---|
| (S)-tert-Butylcarboxamide-piperazine bis [(1S)-camphor-10-sulfonic acid] 15 99.3% de | 0.559 g |
| Potassium tert-butoxide in Tetrahydrofuran 1.72M | 1.25 Ml |
| Methylcyclohexane | 9 mL |

The diastereomerically pure piperazine camphorsulfonic acid salt (15) was suspended in methylcyclohexane and the potassium tert-butoxide/THF solution added. The reaction mixture was heated to 80° C. for 12 hours. Removal of an aliquot indicated that the enantiomeric purity of the piperazine had eroded to 32%.

EXAMPLE 11

Racemization of (S)-2-tert-butylcarboxamide-piperazine bis [(1S)-camphor-10-sulfonic Acid] 15 with Carboxylic Acid

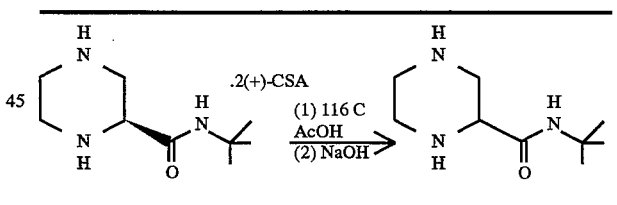

Racemizing Agent = Acetic Acid

| | |
|---|---|
| (S)-tert-Butylcarboxamide-piperazine bis [(1S)-camphor-10-sulfonic acid] 15 99% de | 2.14 g |
| acetic acid glacial | 10 mL |

The diastereomerically pure piperazine camphorsulfonic acid salt (15) was heated in acetic acid at 116° C. for 66 h. After cooling to 25° C., the mixture was diluted with 30 mL THF, adjusted to pH 9.5 with 50% NaOH, and extracted with ethyl acetate (3×50 mL). The organic phases were combined and dried with anhydrous magnesium sulfate and concentrated to give the piperazine amide free base (14). Determination of ee showed an erosion to 71% by chiral HPLC assay.

EXAMPLE 12

Racemization of (R)-2-tert-butylcarboxamide-4-furopicolyl-piperazine with Strong Base

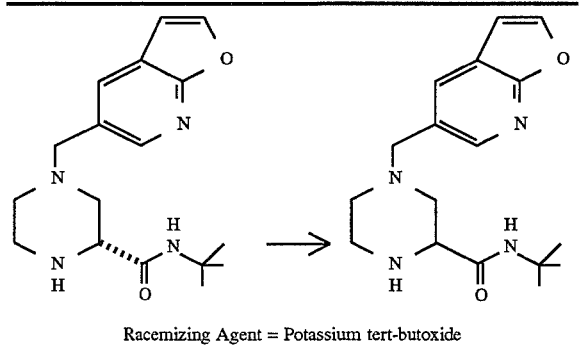

Racemizing Agent = Potassium tert-butoxide

| | |
|---|---|
| (R)-2-tert-butylcarboxamide-4-furopicolyl-piperazine (99.3% ee) | 1.87 g |
| potassium-tert-butoxide 1.7M in THF | 0.02 mL |
| THF | 25 mL |

The enantiomerically pure (R)-2-tert-butylcarboxamide-4-furopicolyl-piperazine is dissolved in THF and potassium-tert-butoxide is added. The solution is heated to reflux for 3 h, when analysis of an aliquot by chiral HPLC indicates that the material is racemic.

EXAMPLE 13

Racemization of (R)-2-tert-butylcarboxamide-4-(3-picolyl)-piperazine with Strong Base

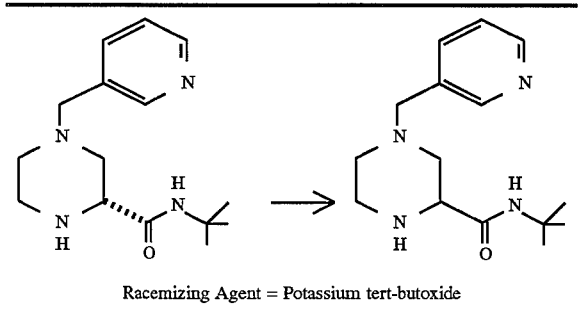

Racemizing Agent = Potassium tert-butoxide

| | |
|---|---|
| (R)-2-tert-butylcarboxamide-4-(3-picolyl)-piperazine (99.3% ee) | 0.67 g |
| potassium-tert-butoxide 1.7M in THF | 0.01 mL |
| THF | 21 mL |

The enantiomerically pure (R)-2-tert-butylcarboxamide-4-(3-picolyl)-piperazine is dissolved in THF and potassium-tert-butoxide is added. The solution is heated to reflux for 4 h, when analysis of an aliquot by chiral HPLC indicates that the material is racemic.

EXAMPLE 14

Combination of Racemisation of (R)-2-tert-butylcarboxamide-piperazine bis (L)-pyroglutamic Acid Salt and Resolution

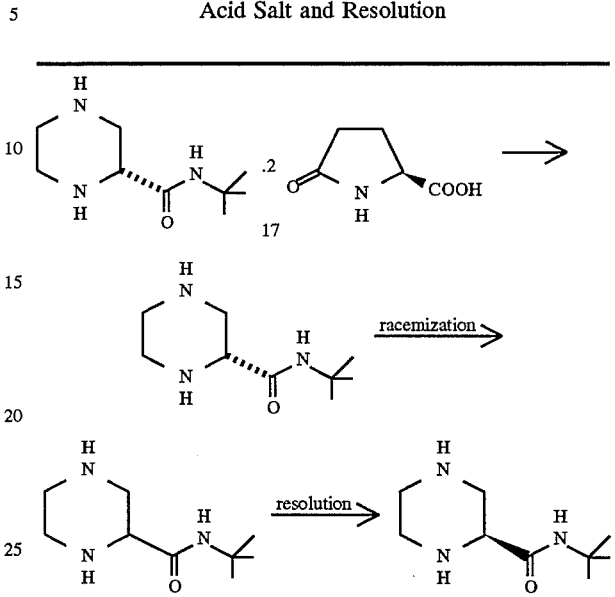

A: Racemization in cyclohexane/THF as the solvent:

| | |
|---|---|
| (R)-2-tert-butylcarboxamide-piperazine bis (L)-pyroglutamic acid salt (17) 97.9% R, 1.03% S, 3.4% TG | 214.98 g (0.468 mol) |
| NaOH 50% aqueous | 80 mL |
| 1-Propanol | 40 mL |
| Water | 65 mL |
| Tetrahydrofuran | 700 mL |
| sat. aqueous K₂CO₃ sol. | 50 mL |
| K-tert-butoxide 1M in tert-butanol | 12.1 mL |

The piperazine bis (L)-pyroglutamic acid salt (undesired (R) enantiomer from Example 5) (17) was dissolved in 1-propanol, H₂O and NaOH in a separatory funnel. To the biphasic system was added 700 mL of THF and the aqueous phase was separated. The organic phase was washed twice with 25 mL sat. aqueous K₂CO₃ solution. The organic solution was transferred to a 1 L 3 neck flask with mechanical stirring and distillation head. At atmospheric pressure, the THF was solvent switched into cyclohexane by concentrating down to a total volume of ca. 250 mL followed by the addition of 700 mL of cyclohexane and reconcentrating to 250 mL. After the addition of 150 mL of THF and potassium-tert-butoxide, the light slurry was heated to reflux for 7 h. The slurry was cooled to 2° C. over 2 h, filtered and washed with 2×40 mL of cyclohexane. After drying, 82.94 g (96% recovery) of a white crystalline powder was Obtained (99.7 wt %, 50.8% R, 49.2% S).

The racemic material can be resolved with 1.8 equiv. of (L)-pyroglutamic acid in a 1-propanol/water medium (see Example 5).

B: Racemisation in 1-propanol as solvent:

| | |
|---|---|
| (R)-Piperazine-2-tert-butyl-carboxamide-bis-L-Pyroglutamic acid salt (17) | 29.62 g (TG = 3.4%) (64.6 mMol) |
| 50% (w/w) aqueous NaOH solution | 11.7 mL |
| Water | 11.7 mL |

-continued

B: Racemisation in 1-propanol as solvent:

| 1-Propanol | 90 mL |
| Sat. aqueous $K_2CO_3$ Sol. | 10 mL |
| K tert-butoxide in THF, 1.72 M | 1.15 mL |

The amine salt (17) was dissolved in a separatory funnel in the water/1-propanol mixture by warming to 40° C. On the addition of NaOH, a second phase formed, which was cut. The aqueous phase was washed twice with 5 mL of saturated aqueous $K_2CO_3$ solution.

An HPLC assay indicated that 95% of the amine was extracted into the organic phase.

The solution of the amine in 1-propanol was charged to a distillation flask, and 200 mL of dry propanol was added. The solution was distilled at atmospheric pressure, until the solvent went over at 98° C. and the KF of an aliquot had fallen to 0.350 mg/mL of solution.

The distillation head was replaced with a reflux condenser and 1.15 mL of a 1.72M solution of K-tert-butoxide was added. The solution was heated to reflux, and chiral analysis of an aliquot indicated that the amine was racemic (50% R, 50% S) after 17 h at reflux. The racemic material can be resolved with 1.8 equiv. of (L)-pyroglutamic acid in a 1-propanol/water medium (see Example 5).

It is equally possible to achieve the same racemisation by the addition of a solution of Na or K-propoxide in 1-propanol.

EXAMPLE 15

Combination of Racemisation of (R)-2-tert-butylcarboxamide-piperazine bis (L)-pyroglutamic Acid Salt (17) and Resolution

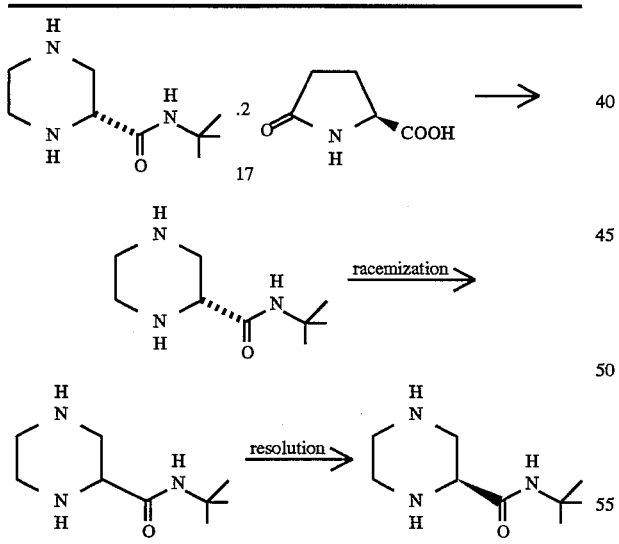

Racemisation in 1-propanol via in situ preparation of the alkoxide:

| (R)-Piperazine-2-tert-butyl-carboxamide-bis-L-Pyroglutamic acid salt (17) | 188.9 g (TG = 3.4%) (0.42 mol) |
| 1-Propanol | 950 mL |
| 50% (w/w) aqueous NaOH solution | 250 g |
| Water | 300 g |

The amine salt (17) was dissolved in the 1-propanol, NaOH, $H_2O$ mixture in a separatory funnel. A lower phase formed and was separated.

The lower aqueous phase contained most of the L-PGA, while the upper 1-propanol phase contained the 79.0 g piperazine (assay by HPLC, 100% recovery). Also present in the organic phase was 4.5 mol % L-PGA and, by HCl titration, 33 mol % NaOH.

The organic phase was azeotropically dried, until the KF of the solution had reached 0.259 mg/mL of solution. At this point, an aliquot was withdrawn and was determined to be racemic (50% R, 50% S).

13.9 g of solid $KHCO_3$ and 50 mL of $H_2O$ were added to the solution at 60° C. and the solution stirred for 30 minutes. A solid phase separated and was removed by filtration.

The remaining 1-propanol solution was free from any strong base at this point and can be resolved using the previously described conditions (see e.g., Example 5).

EXAMPLE 16

1-((R)-2',3'-Epoxypropyl)-(S)-2-tert-butylcarboxamide-4-tert-butoxycarbonyl-piperazine 3

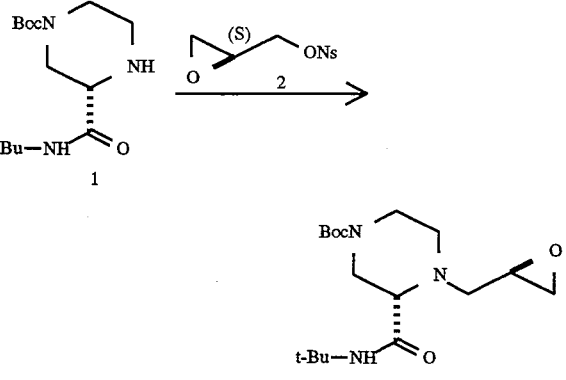

Materials

| (S)-2-tert-butylcarboxamide-4-tert-butoxycarbonyl-piperazine 1 | 11.0 g (38.4 mmol) |
| (2S)-(+)-Glycidyl-3-nitrobenzenesulfonate 2 | 9.96 g (38.4 mmol) |
| Diisopropylethylamine | 5.5 mL (42.2 mmol) |
| DMF | 38 mL |

Piperazine 1 and (2S)-(+)-Glycidyl-3-nitrobenzenesulfonate 2 were dissolved in a 250 mL flask with magnetic stirring under $N_2$ in DMF and DIEA. The resulting homogenous solution was heated to 60°–62° C. for 9 h.

TLC (100% EtOAc as eluent, Ninhydrin stain) indicated complete consumption of piperazine 1.

The reaction was quenched by the addition of 30 mL of a 5% aqueous $NaHCO_3$ solution. The reaction mixture was extracted with 400 mL of isopropyl acetate. The organic phase was washed with water (3×50 mL) and brine (1×50 mL), dried ($Na_2SO_4$) and evaporated to give a yellow oil. Flash chromatography (4 cm×20 cm column, SiO2, gradient elution with 30:70 EtOAc:hexanes to 60:40 EtOAc:hexanes) and evaporation of the product containing fractions gave 9.24 g (71% yield) of 3 as an oil: $[\alpha]_D^{25}=-17.7°$ (c=0.12, MeOH); $^{13}C$ NMR (100 MHz, $CDCl_3$, −25° C., ppm of major rotamer) 170.0, 154.1, 80.2, 66.7, 56.3, 51.7, 50.8, 50.2, 47.0, 44.0, 41.9, 28.3, 28.1.

EXAMPLE 17

Preparation of Epoxide 3 from Piperazine 1 and (S)-Glycidol 4

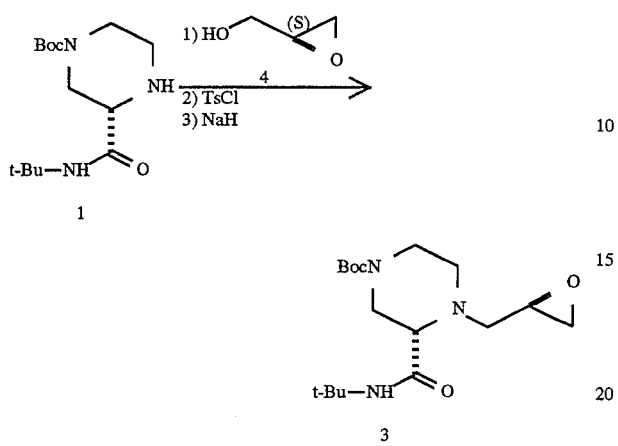

The piperazine 1 (2.00 g, 7.00 mmol) and (S)-glycidol 4 (930 μL, 14.0 mmol) were heated at reflux in 19 mL of isopropanol for 17 h, then the mixture was partitioned with 100 mL of ethyl acetate and 50 mL of water. The layers were separated, and the ethyl acetate layer was washed with saturated sodium chloride, dried with MgSO$_4$, and concentrated to 2.4 g of a gum. A portion of the gum (241 mg) was treated with 2 mL of pyridine and p-toluenesulfonyl chloride (130 mg, 0.68 mmol) overnight, then it was concentrated to an oil. The oil was partitioned with 25 mL of ethyl acetate and 10 mL of water. The ethyl acetate layer was washed with brine, dried (MgSO$_4$) and concentrated to an oil. The crude oil was dissolved in 2 mL of THF and treated with 100 mg of 60% NaH dispersion in oil. After 1 h, the mixture was partitioned with ethyl acetate (50 mL), and 10 mL of water. The ethyl acetate layer was dried with MgSO$_4$ and concentrated to afford the desired epoxide 3 (see previous experimental for spectral data).

EXAMPLE 18

Preparation of Coupled Product 8 from Amide 7 and Epoxide 3

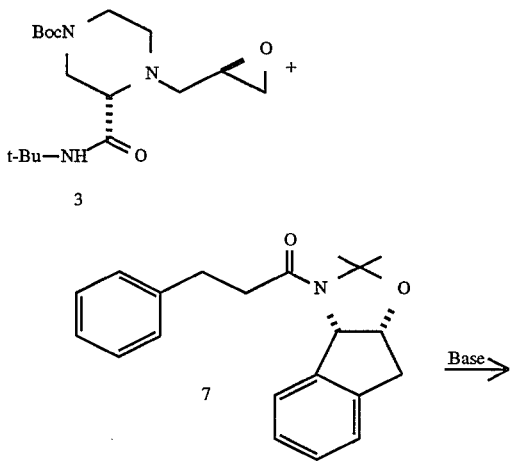

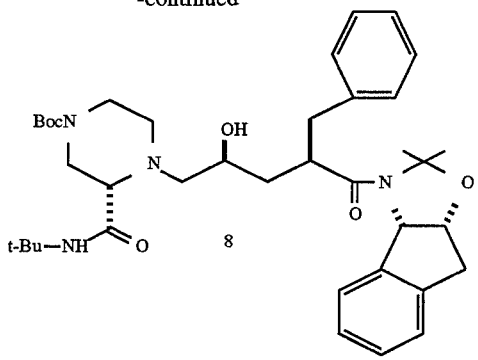

A solution of acetonide 7 (216 mg, 0.67 mmol), which can be made according to the procedure described in U.S. Pat. No. 5,169,952, issued Dec. 8, 1992, and N-Boc-piperazine epoxide 3 (229 g, 0.67 mmol, 1.0 equiv.) in 3.5 mL of THF (KF=22 μg/mL) (KF stands for Karl Fisher titration for water) in a 100 mL round bottom flask, equipped with a thermocouple, magnetic stirrer, and trader nitrogen atmosphere, was cooled to −78° C. Then, n-butyllithium in hexanes solution (0.9 mL, 1.6M, 2.1 equiv.) was added, while keeping the internal temperature between −78° C. to −73° C. The reaction mixture was stirred at −76° C. for 1 h and then allowed to warm to −25° C. over 1 h. The mixture was stirred between −25° to −22° C. for 2.5 h. Then, the reaction mixture was quenched with DI water (5 mL) at −15° C. and partitioned with ethyl acetate (20 mL). The mixture was agitated and the layers were separated. The ethyl acetate extract was washed with saturated NaCl (10 mL) and concentrated under reduced pressure (28" of Hg) to afford crude product which was chromatographed on a silica gel column with ethyl acetate/hexane (3:2) to give the coupled product 8 (84 mg, 20%) as a pale yellow syrup:

$^{13}$C NMR (CDCl$_3$, 75.4 MHz) δ172.6, 170.2, 154.6, 140.8, 140.4, 139.6, 129.5, 128.8, 128.1, 127.2, 126.8, 125.6, 124.1, 96.7, 80.4, 79.2, 65.9, 65.8, 62.2, 51.3, 50.1, 45.3, 43.5, 39.5, 39.1, 36.2, 28.8, 28.4, 26.5, 24.2.

EXAMPLE 19

Preparation of Penultimate 9

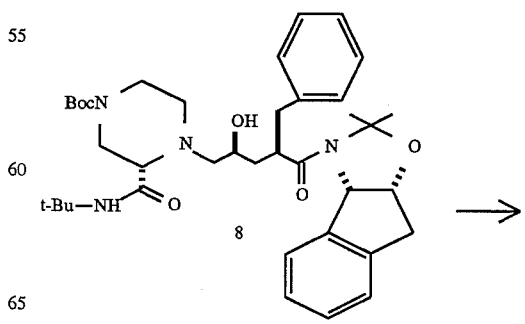

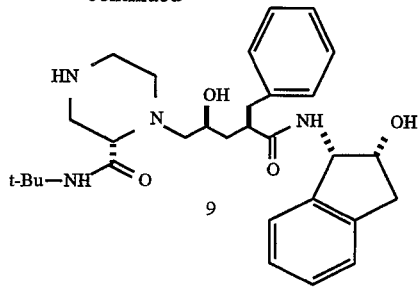

To a solution of compound 8 (5.79 g. 8.73 mmol) in 25.5 mL isopropanol at 0° C. was added 20 ml of 6N aqueous HCl, then 15 minutes later 10 mL of concentrated HCl was added. After 1 hour, the mixture was warmed to 20° C. and aged for 4 hours. The mixture was then cooled to 0° C., and the pH was adjusted to 12.5 with 13 mL of 50% aqueous NaOH, while keeping the temperature ≦29° C. The mixture was extracted with 2×80 mL of EtOAc, and the extracts were dried with MgSO$_4$ and concentrated to afford 5.46 g of the product 9 as a colorless foam:

$^{13}$C NMR (75.4 MHz, CDCl$_3$) δ175.2, 170.5, 140.8, 140.5, 139.9, 129.1, 128.5, 127.9, 126.8, 126.5, 125.2, 124.2, 73.0, 66.0, 64.8, 62.2, 57.5, 49.5, 47.9, 46.4, 45.3, 39.6, 39.3, 38.2, 28.9.

EXAMPLE 20

Preparation of Compound J—Monohydrate

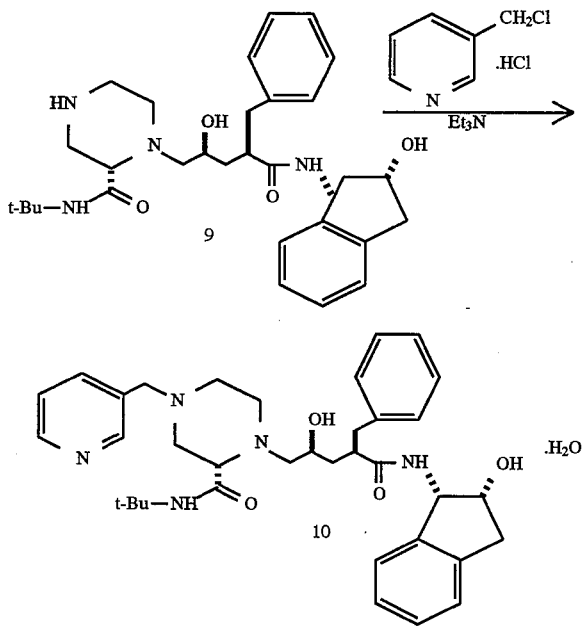

To the solution of 9 in EtOAc (10.5 L, KF=10 mg/mL) from the previous step, was charged with 20 L of sieve dried DMF (KF <30 mg/L) and the mixture was heated with a steam bath under vacuum of 30" of Hg to distill off mainly water and/or any residual isopropanol or ethyl acetate solvent. The final concentrate volume was 13.5 L (KF=1.8 mg/mL) and then triethylamine (2.86 L, 20.51 mol) was added to the 25° C. solution followed by 3-picolyl chloride hydrochloride (96%, g, 7.84 mol). The resulting slurry was heated to 68° C.

The progress of the reaction was followed by HPLC analysis using the same conditions as the previous step. Approximate retention times:

| Retention time (min) | Identity |
|---|---|
| 2.7 | DMF |
| 4.2 | 3-picolyl chloride |
| 4.8 | Compound J |
| 9.1 | penultimate 9 |

The mixture was aged at 68° C. until the residual penultimate compound 9 was <0.3 area % by HPLC analysis. HPLC conditions: 25 cm Dupont C8-RX column, 60:40 acetonitrile/10 mM (KH$_2$PO$_4$/K$_2$HPO$_4$), 1.0 ml/min, detection=220 nm.

The mixture was stirred at 68° C. for 4 h, then cooled to 25° C. and partitioned with ethyl acetate (80 L) and a mixture of 24 L of saturated aqueous NaHCO$_3$ and distilled water (14 L). The mixture was agitated at 55° C. and the layers were separated. The ethyl acetate layer was washed three times with water (20 L) at 55° C. The washed ethyl acetate layer was concentrated at atmospheric pressure to a final pot volume of 30 L. At the end of the atmospheric concentration, water (560 mL) was added to the hot solution and the mixture was cooled to 55° C. and seeded with Compound J monohydrate. The mixture was cooled to 4° C. and filtered to collect the product. The product was washed with cold ethyl acetate (2×3 L), and dried at house vacuum at 25° C. to afford 2905 g (70.7%) of Compound J monohydrate as a white solid.

The differential scanning calorimetric (DSC) curve for Compound J monohydrate at 10° C./min under a nitrogen flow showed a relatively broad, shallow endotherm with a peak temperature of about 66° C. followed by an endotherm-exotherm combination in the temperature range of 129° to 134° C. and finally a major melting endotherm with a peak temperature of 158° C., an extrapolated onset temperature of 155° C. and a corresponding heat of melting of 59 J/g.

EXAMPLE 21

Kinetic Resolution of (S/R)-2-tert-Butylcarboxamide-4-tert-butoxycarbonyl-piperazine 17 to 1

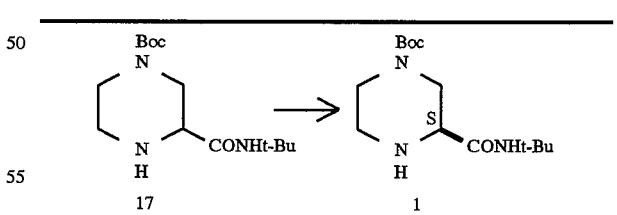

Materials

| | |
|---|---|
| Crude (S/R)-2-tert-Butylcarboxamide-4-tert-butoxycarbonyl piperazine 17 | 1.40 g |
| (S)-2-tert-Butylcarboxamide-4-tert-butoxycarbonyl-piperazine 1 (>99.5% ee) | 4 × 0.14 g |
| Methylcyclohexane with 2% (vol/vol) EtOAc | 14 mL |

The crude, gummy 17 was dissolved in 14 mL of the solvent mixture by heating to 90° C. The solution was allowed to cool, and at 10° C. intervals the solution was seeded with 0.14 g of 1 (>99.5% ee). At 55° C., the fourth 0.14 g batch of seed did not dissolve any more and on further slow cooling to room temperature a white crystalline mass formed. The reaction mixture was filtered, washed with 3 mL of the methylcyclohexane/EtOAc solvent mixture and dried in the vacuum oven under. $N_2$ bleed to give 0.95 g of a white solid. Determination of the enantiomeric purity with a Chiracell AS column showed 93% ee.

The processes and intermediates of this invention are useful for the preparation of end-product compounds that are useful in the inhibition of HIV protease, the prevention or treatment of infection by the human immunodeficiency virus (HIV), and the treatment of consequent pathological conditions such as AIDS. These end-product compounds and their ability to inhibit HIV protease are described in EPO 541, 168, which published on May 12, 1993. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the end-product compounds that can be made from the processes and intermediates of this invention are useful in treating infection by HIV after suspected past exposure to HIV by, e.g., blood transfusion, organ transplant, exchange of body fluids, bites, accidental needle stick, or exposure to patient blood during surgery.

The end-product HIV protease inhibitors are also useful in the preparation and execution of screening assays for antiviral compounds. For example, end-product compounds are useful for isolating enzyme mutants, which are excellent screening tools for more powerful antiviral compounds. Furthermore, such compounds are useful in establishing or determining the binding site of other antivirals to HIV protease, e.g., by competitive inhibition. Thus, the end-product compounds that are made from the processes and intermediates of this invention are commercial products to be sold for these purposes.

HIV protease inhibitor compounds that can be made from the intermediates and processes of the instant invention are disclosed in EPO 541,164. The HIV protease inhibitory compounds may be administered to patients in need of such treatment in pharmaceutical compositions comprising a pharmaceutical carrier and therapeutically effective amounts of the compound or a pharmaceutically acceptable salt thereof. EPO 541,164 discloses suitable pharmaceutical formulations, administration routes, salt forms and dosages for the compounds.

The compounds of the present invention, may have asymmetric centers and occur as racemates, racemic mixtures and as individual diastereomers, or enantiomers with all isomeric forms being included in the present invention.

When any variable (e.g., aryl, heterocycle, R, $R^1$, $R^2$, n, X, etc.) occurs more than one time in any constituent or in formulas I–XI, its definition on each occurrence is independent of its definition at every other occurrence. Also, combinations of substituents and/or variables are permissible only if such combinations result in stable compounds.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl; t-Bu is tert-butyl). As used herein, "aryl" is intended to mean phenyl (Ph) or naphthyl. "Heteroaryl," as used herein, is intended to mean a 6-membered aromatic heterocyclic ring or a stable 8- to 10-membered unsaturated bicyclic heterocycle wherein the mono- or bicyclic-heterocycle consists of carbon atoms and one to three heteroatoms selected from the group consisting of N, O or S. For example, the term "heteroaryl" would include, but is not limited to, the following moieties.

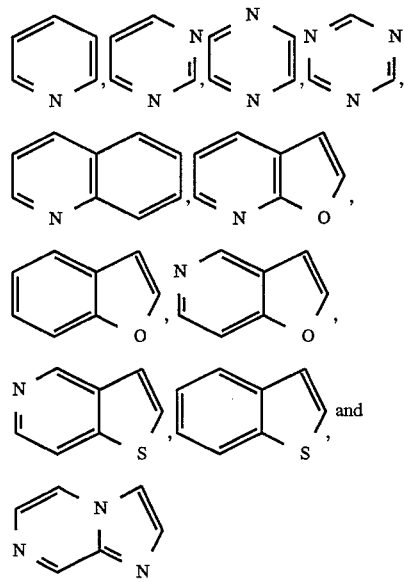

While the foregoing specification teaches the principles of the present invention, with examples provided for the purpose of illustration, it will be understood that the practice of the invention encompasses all of the usual variations, adaptations or modifications, as come within the scope of the following claims and it equivalents.

What is claimed is:

1. A process for racemization of optically pure or enriched piperazine-2-tert-butylcarboxamide substrate of formula IX or X, or a salt thereof,

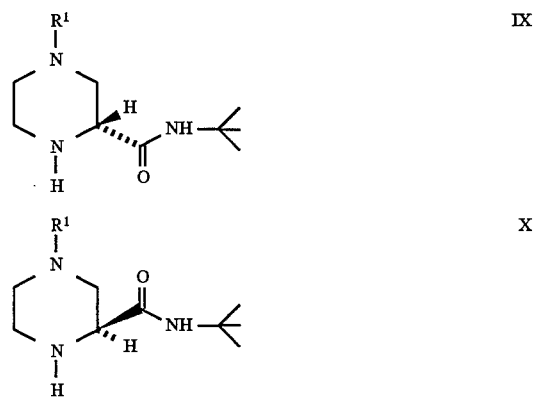

comprising reacting said substrate, or a salt thereof, with a racemizing agent selected from a strong base, an anhydrous metal salt or a carboxylic acid, in a solvent at a temperature range of between room temperature and 250° C.;

wherein

R¹ is

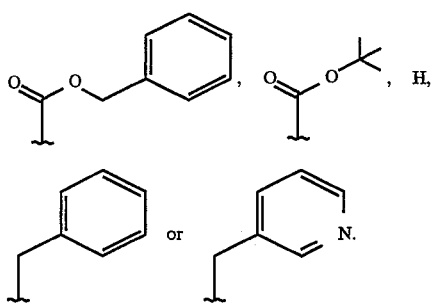

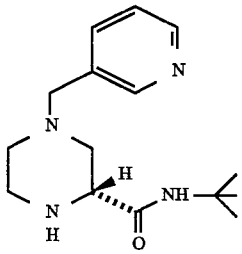

and

-continued or a salt thereof.

2. The process of claim 1, wherein said racemizing agent is a strong base selected from the group consisting of an alkyl lithium, a lithium amide, a hydroxide, an alkoxide and a Schwesinger base.

3. The process of claim 1, wherein said strong base is selected from the group consisting of lithium tert-butoxide, sodium tert-butoxide, potassium tert-butoxide, lithium n-propoxide, sodium n-propoxide, potassium n-propoxide, sodium methoxide, potassium methoxide, sodium ethoxide and potassium ethoxide.

4. The process of claim 1, wherein said racemizing agent is an anhydrous metal salt selected from magnesium chloride, magnesium bromide, zinc chloride, iron (II) chloride or titanium (IV) chloride.

5. The process of claim 1, wherein said racemizing agent is a carboxylic acid selected from acetic acid, propionic acid, butyric acid or isobutyric acid.

6. The process of claim 1, wherein said temperature range is between 50° and 120° C.

7. The process of claim 1, wherein said solvent is an ether, an alkane, a cycloalkane, an alcohol or an aromatic compound, or a mixture thereof.

8. The process of claim 6, wherein said solvent is selected from THF, cyclohexane or propanol, or a mixture thereof.

9. The process of claim 1, wherein said substrate is selected from the group consisting of

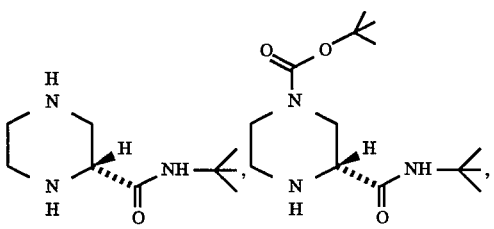

10. The process of claim 8, comprising the additional step of isolating the (S)-enantiomer of the piperazine-2-tert-butylcarboxamide compound from the racemate.

11. The process of claim 1, wherein said salt is selected from a pyroglutamic acid salt or a camphorsulfonic acid salt.

12. The process of claim 10, wherein said salt is the bis-(L)-pyroglutamic acid salt.

13. A process for racemization of an optically pure or enriched piperazine-2-tert-butylcarboxamide substrate of formula IX, or a salt thereof,

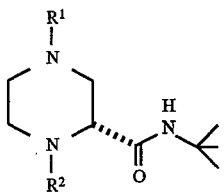

IX comprising reacting said substrate, or a salt thereof, with an alkoxide in 1-propanol at a temperature range of between 50° and 120° C.; wherein R¹ is hydrogen or tert-butyloxycarbonyl; and R² is hydrogen.

14. The process of claim 1, wherein said alkoxide is selected from sodium n-propoxide, potassium n-propoxide and lithium n-propoxide.

15. The process of claim 13, wherein said sodium, potassium or lithium n-propoxide is prepared in situ by the azeotropic drying of sodium, potassium or lithium hydroxide in 1-propanol.

16. The process of claim 12, wherein said salt is the bis-(L)-pyroglutamic acid salt.

17. The process of claim 13, wherein the temperature range is between 85° and 120° C.

* * * * *